United States Patent [19]

Masataka et al.

[11] Patent Number: 4,609,764
[45] Date of Patent: Sep. 2, 1986

[54] PROCESS FOR CONVERTING INACTIVE-TYPE STEREOISOMERS IN SYNTHESIZED SERRICORNIN INTO ACTIVE-TYPE STEROISOMER

[75] Inventors: Mori Masataka; Chuman Tatsuji; Kato Kunio, all of Yokohama; Ono Mikio, Hamura, all of Japan

[73] Assignees: The Japan Tobacco & Salt Public Corporation; Fuji Flavor Company, Limited, both of Japan

[21] Appl. No.: 686,255

[22] Filed: Dec. 26, 1984

[30] Foreign Application Priority Data

Dec. 27, 1983 [JP] Japan ................................. 58-244663

[51] Int. Cl.$^4$ .............................................. C07C 45/79
[52] U.S. Cl. .................................................. 568/384
[58] Field of Search ......................................... 568/384

[56] References Cited

PUBLICATIONS

Ono et al., Agric. Biol. Chem., vol. 44(9), pp. 2259–2260 (1980).
Chuman et al., Agric. Biol. Chem., vol. 43(9), p. 2506 (1979).
Mori et al., Tetrahedron, vol. 38(24), pp. 3705–3711 (1982).

*Primary Examiner*—James H. Reamer
*Attorney, Agent, or Firm*—McGlew and Tuttle

[57] ABSTRACT

Stereoisomers having no cigarette beetle's sex pheromone activity contained in synthesized 4,6-dimethyl-7-hydroxy-nonan-3-one which is an equilibrium mixture of eight stereoisomers may be converted into stereoisomer having said sex pheromone activity by repeating column chromatographic fractionation, epimerization with an acidic or a basic catalyzer and/or racemization with a basic catalyzer in relation to said 3-one compound.

17 Claims, No Drawings

PROCESS FOR CONVERTING INACTIVE-TYPE STEREOISOMERS IN SYNTHESIZED SERRICORNIN INTO ACTIVE-TYPE STEREOISOMER

TECHNICAL FIELD OF THE INVENTION

This invention relates to a process for converting stereoisomers having no sex pheromone activity on the so-called cigarette beetle (referred to as inactive-type hereinafter) contained in synthesized 4,6-dimethyl-7-hydroxy-nonan-3-one which is an equilibrium mixture of stereoisomers into stereoisomer having said sex pheromone activity (referred to as active-type hereinafter).

PRIOR ART

A sex pheromone (i.e. sex attractant) produced by female of the cigarette beetle which has been known as a pest of cured tobacco leaves has recently been isolated and identified as 4,6-dimethyl-7-hydroxy-nonan-3-one (liquid substance) having the undermentioned chemical structure. Lures for controlling said pest have further been developed by using said compound [cf. Chuman et al.: Tetrahedron Letters, 2361(1979); U.S. Pat. No. 4 317 836]. The compound was then called serricornin after the zoological name (i.e. *Lasioderma serricorne F.*) of the cigarette beetle.

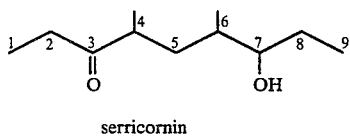

serricornin

As soon as the identification of the structure occurred, serricornin was chemically synthesized in such a manner as being to be industrially applicable [cf. Ono et al.: Agric. Biol. Chem., 44, 2259(1980)].

Having asymmetric carbon atoms at its positions 4, 6 and 7, eight stereoisomers will occur theoretically for the structure of serricornin as above which isomers will be represented as four kinds (or pairs) of optical antipodes from their relative configurations. That is, the following stereostructural formulae (1), (2), (3) and (4) represent stereoisomers of 4S, 6S, 7S- and 4R, 6R, 7R-types (designated merely as <SSS> hereinafter), those of 4R, 6S, 7S- and 4S, 6R, 7R-types (designated merely as <RSS> hereinafter), those of 4R, 6S, 7R- and 4S, 6R, 7S-types (designated merely as <RSR> hereinafter), and those of 4S, 6S, 7R- and 4R, 6R, 7S-types (designated merely as <SSR> hereinafter), respectively [cf. Chuman et al.: Agric. Biol. Chem., 46, 3109(1982)].

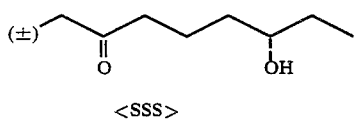

<SSS>

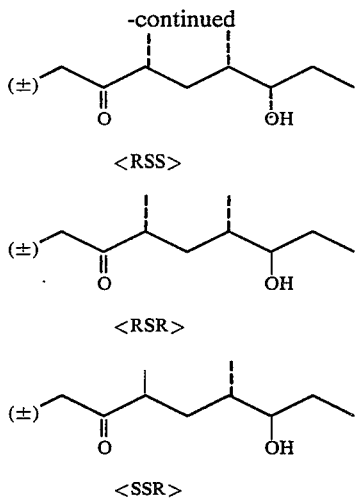

The serricornin obtained by the foregoing synthesizing process of Ono et al. has been recognized to be a mixture of said four optical antipodes in a ratio of approximately 3:1:5:1. However, it has been known further that only the 4S, 6S, 7S-type among the eight stereoisomers of the four optical antipodes is the active-type stereoisomer as defined in the above, the ratio of the said type in the whole amounting accordingly to approximately 1.5/10, while that the abovementioned serricornin having been extracted from cigarette beetle consists of the 4S, 6S, 7S-type stereoisomer alone (cf. Chuman et al.: op. Agric. Biol. Chem.). Thus, it has been a subject in the art to increase the content of the active-type stereoisomer in synthesized serricornin. However, troublesome stages will be necessary to increase the content of the active-type stereoisomer in the product by improving the actual procedures of the synthesizing process, which will be industrially undesirable from the economical viewpoint.

DISCLOSURE OF THE INVENTION

As a result of examining various processes for increasing the activity of synthesized serricornin, we found a process for converting inactive-type stereoisomers contained in synthesized serricornin in a ratio of 8.5/10 of the whole into the active-type stereoisomer. (However, as a pair of optical antipodes is hardly separated from one another generally, the <SSS> as defined in the above will be designated tentatively as active-type stereoisomer in the present specification and claims.)

Specifically, it has been found, with attention focused on the chemical properties of every one of the stereoisomers of serricornin, (1) that the mixture of the stated four components or stereoisomers can be clearly separated into three fractions, <RSR>, <SSS> and <SSR>, and <RSS> by chromatography, (2) that epimerization easily occurs next to the ketone group, namely at the 4 position, with the aid of an acidic or basic catalyzer, and (3) that the treatment of one stereoisomer, for example, the first component <RSR>, with a basic catalyzer containing metallic ions causes racemization into an equilibrium mixture of all the stereoisomers, i.e. the first, second, third and fourth components <RSR>, <SSS>, <SSR>, and <RSS>, respectively.

Accordingly, the present invention provides a process for converting inactive-type stereoisomers in synthesized 4,6-dimethyl-7-hydroxy-nonan-3-one which is an equilibrium mixture of stereoisomers into the active-type stereoisomer, which comprises fractionating said 3-one compound by column chromatography to produce two fractions of inactive-type stereoisomers and a fraction containing an inactive-type stereoisomer as a component, subjecting said fractions of such three kinds of epimerization with an acidic or a basic catalyzer and/or racemization with a basic catalyzer to obtain equilibrium mixtures each containing the active-type stereoisomer as a component, and subjecting said mixtures to column chromatography again to separate fraction(s) of the active-type stereoisomer.

In accordance with the present invention, there is provided a process for simply and inexpensively recycling inactive-type stereoisomers contained essentially as the impurities in serricornin synthesized according to a known process by converting the same into active-type stereoisomers by a combination of a column chromatographic procedure and a catalytic treatment with an acidic or basic catalyzer.

PREFERRED EMBODIMENTS OF THE INVENTION

Synthesized serricornin (liquid substance) prepared by the known process of Ono et al. is subjected to column chromatography using silica gel and a series of solvent mixtures of n-hexane-diethyl ether. That is, by successively increasing the ratio of diethyl ether in the solvent mixture, a fraction of <RSR>, a fraction of a mixture of <SSS> and <SSR> (which are hardly separated) and a fraction of <RSS> are eluted successively. The three kinds of fractions thus produced are then submitted to epimerization and/or racemization.

The epimerization is carried out by using the above <RSS> fraction and/or the fraction of the mixture of <SSS> and <SSR>, whereby equilibrium mixtures each containing the <SSS> as a component are obtained. Particularly, the epimerization with an acidic catalyzer may be conducted as follows: 1 to 5% by weight based on the sample of an acid, preferably acetic, hydrochloric, sulfuric or p-toluenesulfonic acid is added to a sample (i.e. the <RSS> fraction and/or the fraction of mixture of <SSS> and <SSR<), and the resulting mixture is dissolved in a solvent such as water-methanol, water-tetrahydrofuran, dioxane, benzene or chloroform. The solution is either allowed to stand at room temperature or heated at 50° C. or above for 3 to 12 hours. The reaction mixture is neutralized with an aqueous solution of sodium hydrogencarbonate, and then shaken together with a non-polar organic solvent for extraction of the desired materials. The organic layer separated is washed with water and a saturated saline solution successively, and is, after dried with anhydrous magnesium sulfate, concentrated under reduced pressure, whereby equilibrium mixtures each containing <SSS> as a component are obtained.

As for the epimerization with a basic catalyzer, 1 to 5% by weight based on the sample of an amine base, preferably triethylamine, 1,5-diazabicyclo[4.3.0]non-5-ene or 1,8-diazabicyclo[5.4.0]undec-7-ene is added to a sample, and the mixture is dissolved in a polar solvent such as water-methanol, methanol or dimethylformamide, followed by heating the resulting solution under reflux for 3 to 24 hours. Thereafter, the reaction mixture is treated in the same manner as in the epimerization with an acidic catalyzer except that an aqueous solution of ammonium chloride is employed in place of that of sodium hydrogencarbonate for neutralization, whereby equilibrium mixtures each containing <SSS> as a component are obtained.

When the <RSS> fraction is used as the material of the epimerization, the equilibrium mixture consists of <SSS> and <RSS>, while it consists of <SSS>, <RSS>, <RSR> and <SSR> when the fraction of mixture of <SSS> and <SSR> is used as the material of the epimerization.

The both equilibrium mixtures are then subjected to column chromatography again, whereby an <SSS> fraction may be separated from the equilibrium mixture of <SSS> and <RSS>, while three kinds of fractions similar to those having been produced by the column chromatography of the synthesized serricornin described above may be produced from the equilibrium mixture of <SSS>, <RSS>, <RSR> and <SSR>, from which three kinds of fractions an <SSS> fraction will be able to separate finally.

On the other hand, the racemization in the process of the present invention is carried out by using the <RSR> fraction and/or the <RSS> fraction both having been produced by the foregoing column chromatography of the synthesized serricornin, whereby an equilibrium mixture of <SSS>, <RSS>, <RSR> and <SSR> is obtained. That is, 1 to 20% by weight based on the sample of a metal hydroxide, a basic metal salt or a metal alkoxide, preferably potassium or sodium hydroxide, potassium carbonate, sodium methoxide, potassium t-butoxide or aluminum t-butoxide is added to a sample (i.e. the <RSR> fraction and/or the <RSS> fraction), and the mixture is dissolved in a polar solvent, preferably methanol, ethanol, water-methanol or dimethylformamide, followed by heating the resulting solution under reflux for 1 to 5 days. Thereafter, the reaction mixture is treated in the same manner as in the epimerization with a basic catalyzer, whereby an equilibrium mixture consisting of <SSS>, <RSS>, <RSR> and <SSR> is obtained. The mixture is subjected to column chromatography similar to that of the synthesized serricornin as described above to thereby produce three kinds of fractions, from which will be able to separate an <SSS> fraction finally.

As described above, it is possible to convert most of inactive-type stereoisomers contained in synthesized serricornin into the active-type stereoisomer by repeating column chromatographic fractionation, epimerization and racemization according to the present invention.

To further illustrate the present invention, and not by way of limitation, the following examples will be given.

EXAMPLE 1

Twenty grams of synthesized serricornin (liquid substance) prepared by the process of Ono et al. were charged into a column packed with 100 g of silica gel and then eluted with 200 ml portions of a series of solvent mixtures of n-hexane-diethyl ether successively.

A small amount of low-polarity impurities was eluted with n-hexane alone first. Subsequently, 9 g of an <RSR> fraction were eluted with n-hexane-diethyl ether (95:5), then 8 g of a fraction of a mixture of <SSS> and <SSR> (in a ratio of approximately 3:1) were eluted with n-hexane-diethyl ether(3:1), and finally 1.5 g of an <RSS> fraction were eluted with n-hexane-diethyl ether(1:1). The totalling yield corresponded to 98% of the synthesized serricornin used.

To the whole <RSS> fraction above (i.e. 1.5 g) were added 50 mg of p-toluenesulfonic acid, and the mixture was dissolved in 10 ml of water-tetrahydrofuran(1:4), followed by heating the resulting solution at 50° C. for 5 hours. The reaction mixture was cooled, neutralized with a saturated aqueous solution of sodium hydrogencarbonate, and then shaken together with 5 ml portions of diethyl ether twice for extraction of the desired materials. The combined organic layer was washed with 5 ml portions of water and of a saturated saline solution successively, and was, after dried with anhydrous magnesium sulfate, concentrated under reduced pressure, whereby 1.4 g (corresponding to 93% of the <RSS> fraction) of an equilibrium mixture consisting of <SSS> and <RSS> in a ratio of approximately 4:1 were obtained.

The equilibrium mixture was subjected to column chromatography with 5 g of silica gel, and 1.1 g (73% of the same as above) of an <SSS> fraction were eluted with 10 ml of n-hexane-diethyl ether(3:1). Subsequently, 0.3 g (20% of the same as above) of an <RSS> fraction were eluted with 10 ml of n-hexane-diethyl ether(1:1).

EXAMPLE 2

One and a half grams of an <RSS> fraction having been produced by the column chromatography which was accomplished in the same manner as that of the synthesized serricornin described in Example 1 and 50 mg of triethylamine were dissolved in 10 ml of water-methanol, and the resulting solution was heated under reflux overnight. Thereafter, the reaction mixture was treated in the same manner as in Example 1 except that a saturated aqueous solution of ammonium chloride was employed in place of that of sodium hydrogencarbonate for neutralization, whereby 1.5 g (corresponding to 100% of the <RSS> fraction) of an equilibrium mixture consisting of <SSS> and <RSS> in a ratio of approximately 3:1 were obtained.

The equilibrium mixture was subjected to column chromatography similar to that in Example 1, whereby 1.0 g (67% of the same as above) of an <SSS> fraction and 0.4 g (27% of the same as above) of an <RSS> fraction were eluted successively.

EXAMPLE 3

Nine grams of the <RSR> fraction having been produced by the column chromatography of the synthesized serricornin in Example 1 together with 500 mg of potassium hydroxide were dissolved in 100 ml of water-methanol(3:2), and the resulting solution was heated under reflux for 2 days. Thereafter, the reaction mixture was treated in the same manner as in Example 2 except that 50 ml portions of the same solvent for extraction and of the same liquids for washing were employed in place of the 5 ml portions of the solvent for extraction and of the liquids for washing, whereby 8.6 g (corresponding to 96% of the <RSR> fraction) of an equilibrium mixture consisting of <SSS>, <RSS>, <RSR> and <SSR> in a ratio of approximately 4:1.5:3.5:1 were obtained.

The equilibrium mixture was subjected to column chromatography similar to that of the synthesized serricornin described in Example 1, whereby 2.8 g (31% of the same as above) of an <RSR> fraction, 4.4 g (49% of the same as above) of a fraction of a mixture of <SSS> and <SSR>, and 1.1 g (12% of the same as above) of an <RSS> fraction were eluted successively.

EXAMPLE 4

Nine grams of an <RSR> fraction and 1.5 g of an <RSS> fraction both having been produced by the column chromatography which was accomplished in the same manner as that of the synthesized serricornin described in Example 1 were combined, and 500 mg of sodium hydroxide were added thereto. The resulting mixture was dissolved in 100 ml of water-methanol(3:2), and the solution was heated under reflux for 2 days. Thereafter, the reaction mixture was treated in the same manner as in Example 3, whereby 10.3 g (corresponding to 98% of the total of the <RSS> and <RSR> fractions) of an equilibrium mixture consisting of <SSS>, <RSS>, <RSR> and <SSR> in a ratio of approximately 3.8:1.3:3.9:1.0 were obtained.

The equilibrium mixture was subjected to column chromatography similar to that of the synthesized serricornin in Example 1, whereby 4 g (38% of the same as above) of an <RSR> fraction, 4.9 g (47% of the same as above) of a fraction of a mixture of <SSS> and <SSR>, and 1.3 g (12% of the same as above) of an <RSS> fraction were eluted successively.

EXAMPLE 5

Eight grams of the fraction of the mixture of <SSS> and <SSR> having been produced by the column chromatography of the synthesized serricornin in Example 1 together with 400 mg of triethylamine were dissolved in 100 ml of water-methanol(2:3), and the solution was heated under reflux for 5 hours. Thereafter, the reaction mixture was treated in the same manner as in Example 3, whereby 7.8 g (corresponding to 98% of the fraction of the mixture of <SSS> and <SSR>) of an equilibrium mixture consisting of <SSS>, <RSS>, <RSR> and <SSR> in a ratio of approximately 11:4:4:1 were obtained.

The equilibrium mixture was subjected to column chromatography similar to that of the synthesized serricornin in Example 1, whereby 1.5 g (19% of the same as above) of an <RSR> fraction, 4.4 g (55% of the same as above) of a fraction of a mixture of <SSS> and <SSR> in a ratio of approximately 11:1, and 1.4 g (18% of the same as above) of an <RSS> fraction were eluted successively.

What is claimed is:

1. Process of treating the synthesized compound 4,6-dimethyl-7-hydroxy-nonan-3-one, which is an equilibrium mixture of stereoisomers including three inactive-type stereoisomers having no sex pheromone activity on the cigarette beetle and an active-type stereoisomer having said sex pheromone activity, for converting said inactive-type stereoisomers to said active-type stereoisomer, which comprises the steps of:

(a) fractionating said compound by column chromatography using a column material capable of retaining said stereoisomers thereon, and thereafter successively a series of three solvent mixtures containing a first solvent and a second solvent, capable of removing from the column the stereoisomers so retained by the column material, and in which the ratio of the second solvent to the first solvent in the solvent mixture is selectively increased successively, and sufficient for thereby selectively producing three successive column fractions including (a-1) a first fraction containing a first said inactive-type stereoisomer and capable of undergoing racemization to form an equilibrium mixture of stereoisomers containing said active-type stereoisomer, (a-2) a second fraction containing said active-type stereoisomer and a second said inactive-type stereoisomer and capable of undergoing epimerization to form an equilibrium mixture of stereoisomers containing said active-type stereoisomer, and (a-3) a third fraction containing a third said inactive-type stereoisomer and capable of undergoing racemization to form an equilibrium mixture of stereoisomers containing said active-type stereoisomer and also capable of undergoing epimerization to form an equilibrium mixture of stereoisomers containing said active-type stereoisomer, (b) subjecting the first fraction to said racemization, the second fraction to said epimerization and the third fraction to one of said racemization or said epimerization, thereby to form the corresponding said equilibrium mixture of stereoisomers each containing said active-type stereoisomer, and (c) fractionating each said equilibrium mixture obtained in step (b) by column chromatography according to step (a) using successively a series of said solvent mixtures in successively selectively increased ratios of said second solvent to said first solvent, and sufficient for thereby selectively producing in each case corresponding successive fractions including an active-type stereoisomer rich fraction.

2. Process of claim 1, wherein
step (b) is carried out such that
(b-1) the racemization of the first fraction forms an equilibrium mixture containing said first, second, and third inactive-type stereoisomers and said active-type stereoisomer, (b-2) the epimerization of said second fraction forms an equilibrium mixture containing said first, second and third inactive-type stereoisomers and said active-type stereoisomer and rich in said active-type stereoisomer relative to the content of said second inactive-type stereoisomer, and (b-3i) where the third fraction is subjected to racemization it forms an equilibrium mixture containing said first, second and third inactive-type stereoisomers and said active-type stereoisomer, whereas (b-3ii) where the third fraction is subjected epimerization it forms an equilibrium mixture containing said third inactive-type stereoisomers and said active-type stereoisomers, and (c) is carried out such that a series of said solvent mixtures is used concordantly for thereby selectively producing (c-1) from each said equilibrium mixture containing said fist, second and third inactive-type stereoisomers and said active-type stereoisomer from step (b), successive column fractions including a first fraction containing said first inactive-type stereoisomer and capable of undergoing said racemization, a second fraction containing said active-type stereoisomer and said second inactive-type stereoisomer and rich in said active-type stereoisomer relative to the content of said second inative-type stereoisomer and capable of undergoing said epimerization for further enrichment of said active-type stereoisomer relative to the content of said second inactive-type stereoisomer, and a third fraction containing said third inactive-type stereoisomer and capable of undergoing said raceimzation and also capable of undergoing said epimerization, and (c-2) from said equilibrium mixture containing said third inactive-type stereoisomer and said active-type stereoisomer from step (b), a first fraction of thereby separated said active-type stereoisomer and a second fraction containing said third inactive-type stereoisomer and capable of undergoing said racemization and also capable of undergoing said epimerization.

3. Process of claim 1 wherein step (b) is carried out such that the third fraction is subjected to said racemization.

4. Process of claim 1, wherein step (b) is carried out such that the first fraction and the third fraction are combined and together subjected to said racemization.

5. Process of claim 1, wherein step (b) is carried out such that the third fraction is subjected to said epimerization.

6. Process of claim 1, wherein said racemization is carried out with a basic catalyzer and said epimerization is carried out with an acidic or basic catalyzer.

7. Process of claim 1, wherein said racemization is carried out with a basic catalyzer in the form of at least one member selected from the group consisting of a metal hydroxide, a basic metal salt and a metal alkoxide, and said epimerization is carried out with an acidic catalyzer in the form of an acid or a basic catalyzer in the form of an amine base.

8. Process of claim 1, wherein said first solvent is n-hexane and said second solvent is diethyl ether.

9. Process of claim 8, wherein said first and second solvents are used in the substantial ratios of the first solvent to the second solvent successively correspondingly of
- 95:5 for removing initially from the column a fraction containing any said first inactive-type stereoisomer,
- 3:1 for removing from the column a fraction containing said active-type stereoisomer and any said second inactive-type stereoisomer, and
- 1:1 for removing finally from the column a fraction containing said third inactive-type stereoisomer.

10. Process of claim 9, wherein the column material used in the column is silica gel.

11. Process of claim 1, wherein said compound is an equilibrium mixture of four pairs of optical antipodes comprising
   (1) stereoisomers of the 4R, 6S, 7R- and 4S, 6R, 7S-types, and constituting said first inactive-type stereoisomer,
   (2) stereoisomers of the 4S, 6S, 7S- and 4R, 6R, 7R-types, and constituting said active-type stereoisomer,
   (3) stereoisomers of the 4S, 6S, 7R- and 4R, 6R, 7S-types, and constituting said second inactive-type stereoisomer, and
   (4) stereoisomers of the 4R, 6S, 7S- and 4S, 6R, 7R-types, and constituting said third inactive-type stereoisomer.

12. Process of treating the synthesized compound 4,6-dimethyl-7-hydroxy-nonan-3-one, which is an equilibrium mixture of stereoisomers including first, second, third and fourth components, said first, third and fourth components constituting three inactive-type stereoisomers having no sex pheromone activity on the cigarette beetle and said second component constituting an active-type stereoisomer having said sex pheromone activity, for converting said first, third and fourth components to said second component, which comprises the steps of
   (a) fractionating said compound by column chromatography using silica gel as column material, and thereafter successively a series of three solvent mixtures containing n-hexane as a first solvent and diethyl ether as a second solvent, in which the ratio of the second solvent to the first solvent in the solvent mixture is selectively increased successively, and sufficient for thereby producing three successive column fractions including
      (a-1) a first fraction containing said first component and capable of undergoing racemization with a basic catalyzer to form an equilibrium mixture containing said four components,
      (a-2) a second fraction containing said second and third components and capable of undergoing epimerization with an acidic or basic calalyzer to form an equilibrium mixture containing said four components and rich in said second component relative to the content of said third component, and
      (a-3) a third fraction containing said fourth component and capable of undergoing racemization with a basic catalyzer to form an equilibrium mixture containing said four components and also capable of undergoing epimerization with an acidic or basic catalyzer to form an equilibrium mixture containing said second and fourth components,
   (b) subjecting the first fraction to said racemization, the second fraction to said epimerization and the third fraction to one of said racemization or said epimerization, thereby to form the corresponding said equilibrium mixture, and
   (c) fractionating each said equilibrium mixture obtained in step (b) by column chromatography according to step (a) using successively a series of said solvent mixtures in successively selectively increased ratios of said second solvent to said first solvent, and sufficient for thereby selectively producing in each case corresponding successive fractions including
      (c-1) from each said equilibrium mixture containing said four components from step (b) a first fraction containing said first component and capable of undergoing said racemization, a second fraction containing said second and third components and rich in said second component relative to the content of said third component and capable of undergoing said epimerization for further enrichment of said second component relative to the content of said third component, and a third fraction containing said fourth component and capable of undergoing said racemization and also capable of undergoing said epimerization, and
      (c-2) from said equilibrium mixture containing said second and fourth components from step (b) a first fraction of thereby separated said second component and a second fraction containing said fourth component and capable of undergoing said racemization and also capable of undergoing said epimerization.

13. Process of claim 12, wherein step (b) is carried such that the third fraction is subjected to said racemization.

14. Process of claim 12, wherein step (b) is carried out such that the first fraction and the third fraction are combined and together subjected to said racemization.

15. Process of claim 12, wherein step (b) is carried out such that the third fraction is subjected to said epimerization.

16. Process of claim 12, wherein said first and second solvents are used in the substantial ratios of the first solvent to the second solvent successively correspondingly of
- 95:5 for removing initially from the column a fraction containing any said first component,
- 3:1 for removing from the column a fraction containing said second and third components, and
- 1:1 for removing finally from the column a fraction containing said fourth component.

17. Process of claim 12, wherein said compound is an equilibrium mixture of four pairs of optical antipodes comprising
   (1) stereoisomers of the 4R, 6S, 7R- and 4S, 6R, 7S-types, and constituting said first component,
   (2) stereoisomers of the 4S, 6S, 7S- and 4R, 6R, 7R-types, and constituting said second component,
   (3) stereoisomers of the 4S, 6S, 7R- and 4R, 6R, 7S-types, and constituting said third component, and
   (4) stereoisomers of the 4R, 6S, 7S, -and 4S, 6R, 7R-types, and constituting said fourth component.

* * * * *